United States Patent [19]

Ryles

[11] Patent Number: 5,658,257

[45] Date of Patent: Aug. 19, 1997

[54] SYRINGE

[75] Inventor: Louis Ryles, Gold Coast, Australia

[73] Assignee: Medical Plastics (AUST) Pty. Ltd., Australia

[21] Appl. No.: 129,172

[22] PCT Filed: Apr. 21, 1992

[86] PCT No.: PCT/AU92/00178

§ 371 Date: Oct. 18, 1993

§ 102(e) Date: Oct. 18, 1993

[87] PCT Pub. No.: WO92/18186

PCT Pub. Date: Oct. 29, 1992

[30] Foreign Application Priority Data

Apr. 17, 1991 [AU] Australia .................... PK5665

[51] Int. Cl.⁶ .................................................. A61M 5/32
[52] U.S. Cl. ........................ 604/195; 604/110; 604/178; 604/187
[58] Field of Search .................... 604/195, 192, 604/198, 196, 263, 110, 187, 207, 220, 166, 208–211, 224, 228, 240, 241, 242, 272

[56] References Cited

U.S. PATENT DOCUMENTS

| | | | |
|---|---|---|---|
| 4,826,490 | 5/1989 | Byrne et al. | 604/198 |
| 4,932,945 | 6/1990 | Braginetz et al. | 604/195 |
| 4,950,241 | 8/1990 | Ranford | 604/110 |
| 5,049,133 | 9/1991 | Villen Pascual | 604/110 |
| 5,057,087 | 10/1991 | Harmon | 604/198 |
| 5,088,987 | 2/1992 | Noonan, Jr. | 604/195 |
| 5,256,151 | 10/1993 | Chul | 604/195 |

FOREIGN PATENT DOCUMENTS

| | | | |
|---|---|---|---|
| 9107198 | 11/1990 | WIPO | 604/187 |
| 9103269 | 3/1991 | WIPO | 604/110 |

*Primary Examiner*—Corrine M. Maglione
*Assistant Examiner*—V. Alexander
*Attorney, Agent, or Firm*—Hoffman, Wasson & Gitler, P.C.

[57] ABSTRACT

A syringe for administering a medicament having a barrel provided with a needle attachment member to which a needle may be mounted and which is retained by a catch at one end of the barrel, and a plunger which is movable in the barrel to expel medicament through the needle attachment member and needle. The plunger is hollow and contains a vacuum and is provided with a gripping member at one end which closes one end of the plunger and which when the plunger is advanced can engage the needle attachment member to releases its catch and withdraw the needle attachment member and mounted needle into the plunger.

13 Claims, 4 Drawing Sheets

SYRINGE

FIELD OF THE INVENTION

This invention relates to a safety syringe and in particular to a single use syringe having provision for retraction of a hypodermic needle into the body of the syringe.

BACKGROUND ART

With the advent of contagious diseases such as AIDS and Hepatitis B, the possibility of so called "needle stick" injuries in the medical environment has proliferated along with many and varied arrangements for preventing accidental infection of medical workers as a result of this type of injury. In addition, the proliferation of intravenous drug use has resulted in discarded syringes and needles on beaches and other areas where a passer-by can inadvertently step on a needle and also be infected.

As a result of this, there has been a proliferation of proposals for single use disposable syringes whereby a needle is retracted into the body of the syringe after a single use. However, most of these arrangements involve complete reworking of the conventional disposable syringe construction in such a way that the conventional luer lock disposable needle fitments are done away with such that the arrangements proposed are too complex and too expensive. Many also require additional manual steps to retract the needle.

A typical example of the prior art is U.S. Pat. No. 4,995,870 which describes a safety syringe where the needle has a barb on the end inside the syringe for engaging the syringe plunger when the plunger is depressed to inject its contents into a patient. Once the barb engages the plunger the operator unlocks the needle and then withdraws the plunger to retract the needle into the syringe. The needle used is not a conventional luer lock fitment as it must have a barb on the end and the retraction process requires two manual steps which expose the operator of the syringe to the risk of "needle stick" injuries and are time-consuming and inconvenient.

A number of automatically retracting syringes have therefore been proposed. These include spring-loaded devices such as that described in U.S. Pat. No. 4,929,237 where a pushing force applied to the proximal end of the syringe moves the syringe within a housing against a spring to an operative position and releasing the pushing force allows the syringe to retract proximally drawing the needle back into the housing. The syringe is complex and likely to be expensive.

Australian Application No. 66,363/90 discloses a syringe where the plunger captures the needle and the plunger is withdrawn by a return spring when the downward pressure on it is released, thereby retracting the needle. The specification at page 6, line 22 refers to withdrawing the entire plunger and the attached needle back into the barrel of the syringe using a vacuum, but proposes no feasible way to do this. The only embodiments described use a return spring and the snap lock engagement means used to secure the needle to the plunger leaves a very large space (best seen in FIG. 3) in which medicament will remain when the plunger is withdrawn. The medicament is then likely to leak, creating a contamination hazard.

A vacuum-retractable syringe is proposed in Australian Application No. 70,672/91 where the needle is withdrawn into the interior of a hollow plunger under force of a vacuum within the plunger, however, in that invention the thrust exerted by the operator of the syringe must be sufficient to cause a washer at the end of travel of the plunger to rupture and to push a plug down through the washer to engage the needle. The needle mount (which is not a conventional luer lock) must also rupture so that the plug can withdraw the needle under vacuum into the plunger, where it is held in place by magnets. The syringe is complicated and unlikely to be feasible due to its complex operation.

These proposals have not found ready acceptance in the medical profession because of cost and inconvenience.

DISCLOSURE OF THE INVENTION

According to the present invention there is provided a syringe for administering medicaments comprising:

an elongate barrel for holding the medicament having a proximal and distal end;

a hollow plunger having a closed proximal end protruding from the proximal end of the barrel and a distal end located within the barrel, said plunger being slidably mounted in said barrel and having vacuum means in its interior;

a retractable needle attachment member adapted to receive a hypodermic needle contiguous with the distal end of said barrel and so arranged that operation of said plunger causes medicament to be expelled from within said barrel through the hypodermic needle; and needle attachment member gripping means constituting a closure of the distal end of said plunger and being adapted to engage the needle attachment member so that the needle attachment member can be retracted into the interior of said plunger by the vacuum within said plunger.

The retractable needle attachment member preferably protrudes from the distal end of the barrel into a retaining shoulder attached to the barrel and has a portion adapted so that a conventional luer lock hypodermic needle can be releasably attached to the syringe and medicament can be expelled through the retractable needle attachment member and through the needle as the plunger as forced toward the distal end of the barrel.

Advantageously, the needle attachment member is operatively secured in the retaining shoulder and therefore to the distal end of the barrel by a releasable catch which is released when the plunger as pushed home to expel the contents of the syringe through the hypodermic needle. The catch preferably comprises an annular shoulder on an internal wall of the retaining shoulder adjacent the distal end of the barrel which co-operates with an outwardly biased finger protruding from a side wall of the needle attachment member. Advantageously, as a consequence of the engagement between the annular shoulder and the biased finger, the needle attachment member is biased into sealing engagement with the barrel at longitudinally spaced sealing sites while the retractable needle attachment member is a slide fit rather than a friction fit in the distal end of the barrel.

It is particularly preferred that the biased finger includes a protrusion that engages the annular shoulder and a portion of reduced thickness distally adjacent the protrusion constituting a pivot point for the biased finger so that the biased finger bends outwardly maintaining the engagement of the projection with the annular shoulder when the needle attachment means is subject to force in the proximal direction. A significant force in the proximal direction is generated when the needle of a syringe is pushed into the patient. When the pivot point of the biased finger is located adjacent the projection this force serves to hold the needle attachment member more tightly in the retaining shoulder but, if it were spaced further from the projection would tend to cause the needle attachment means to dislodge.

The retractable needle attachment member gripping means preferably releases the needle attachment member when the plunger is pushed home so that it can be drawn back into the syringe along with the exposed needle. Advantageously, the gripping means includes a catch release mechanism adapted to engage the biased finger on the needle attachment member and release the biased finger from engagement with the annular shoulder so that the needle attachment means engages the gripping means and is released from the retaining shoulder, whereby the gripping means disengages from the distal end of the plunger and the gripping means in operative engagement with the needle attachment means is retracted into the interior of said plunger by the vacuum within said plunger. Preferably, the catch release mechanism comprises a claw member including a leading camming surface and a trailing shoulder, the trailing shoulder being adapted to engage the distal face of the plunger and the camming surface being adapted to abut an inside surface of the retaining shoulder, whereby the claw member is urged to bend inwardly with the camming surface engaging the biased finger and the trailing shoulder disengaging the distal face of the plunger.

If the vacuum fails for some reason to retract the needle, it is preferred that the syringe be arranged so that the needle can be retracted manually by retracting the plunger. Preferably, the gripping means includes first annular beading adjacent its proximal end and the plunger includes second annular beading on its inside surface adjacent the distal end of the plunger, wherein on manual withdrawal of the plunger in the proximal direction the second annular beading on the plunger engages the first annular beading on the gripping means allowing the gripping means and operatively engaged needle attachment means to be withdrawn into the barrel in the event that the vacuum retraction fails.

A further safety feature of the present invention is that the syringe cover may be adapted to close the opening left by retraction of the needle attachment member.

BRIEF DESCRIPTION OF THE DRAWINGS

In order that the present invention can be more readily understood and be put into practical effect, reference will now be made to the accompanying drawings and wherein.

DESCRIPTION OF THE PREFERRED EMBODIMENT

Figure 1:
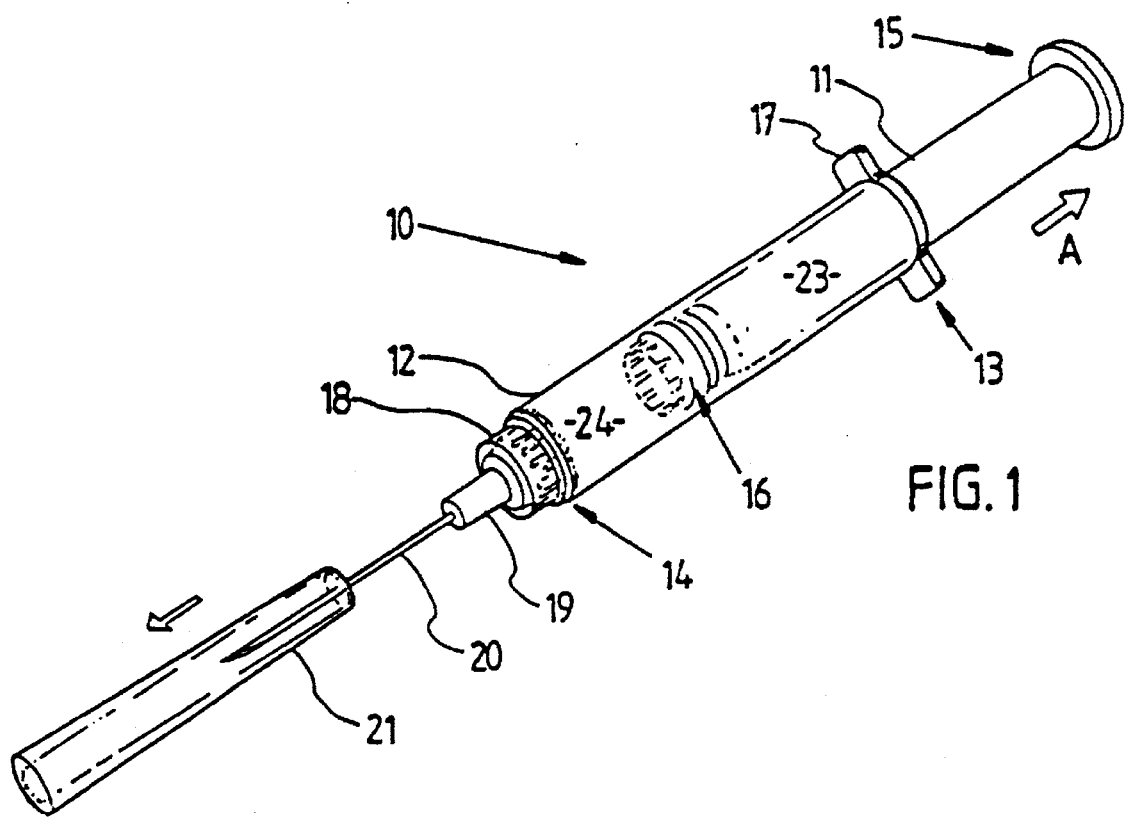
FIG. 1 is a perspective view of a syringe in accordance with one embodiment of the invention, FIG. 2 a view similar to FIG. 1 showing the needle in the retracted position after use.

As seen in FIG. 1, the syringe 10 comprises a hollow evacuated plunger 11 slidably mounted within an elongated barrel 12 which as a proximal end 13 and a distal end 14. The hollow plunger 11 has a proximal end 15 protruding from the proximal end 13 of the barrel 12 and a distal end 16 axially slidable within the barrel 12. The plunger 11 (or at least at a portion of it towards its distal end) is hollow and a chamber 25 inside plunger 11 as evacuated so that there is a vacuum inside the plunger. The barrel 12 has a flange 17 at its proximal end 13 that is gripped by the operator when using the syringe 10. At its distal end 14, the barrel 12 has a retaining shoulder 18 which retains the needle attachment member 26. The hypodermic needle 20 has a lock 19 by means of which the needle is attached to the member 26 and the arrangement is preferably a conventional luer lock hypodermic needle. The needle 20 is covered by protective cover 21 until just prior to use so that accidental puncture injuries cannot occur.

The syringe 10 in FIG. 1 is shown with cover 21 partially removed. When the cover 21 is removed, plunger 11 is pulled back in the direction of arrow A to draw a medicament (not shown) through needle 20 into the space 24 in the barrel 12. The barrel 12 (which may have a graduated volume scale marked thereon) is about half full in FIG. 1. Further movement of the plunger 11 in the direction of arrow A will continue the filling of the barrel 12 and, once the desired volume of medicament has been drawn into the barrel 12 and needle 20 has been inserted into a patient, the medicament can be expelled by depressing the plunger in the direction opposite to arrow A.

Figure 2:
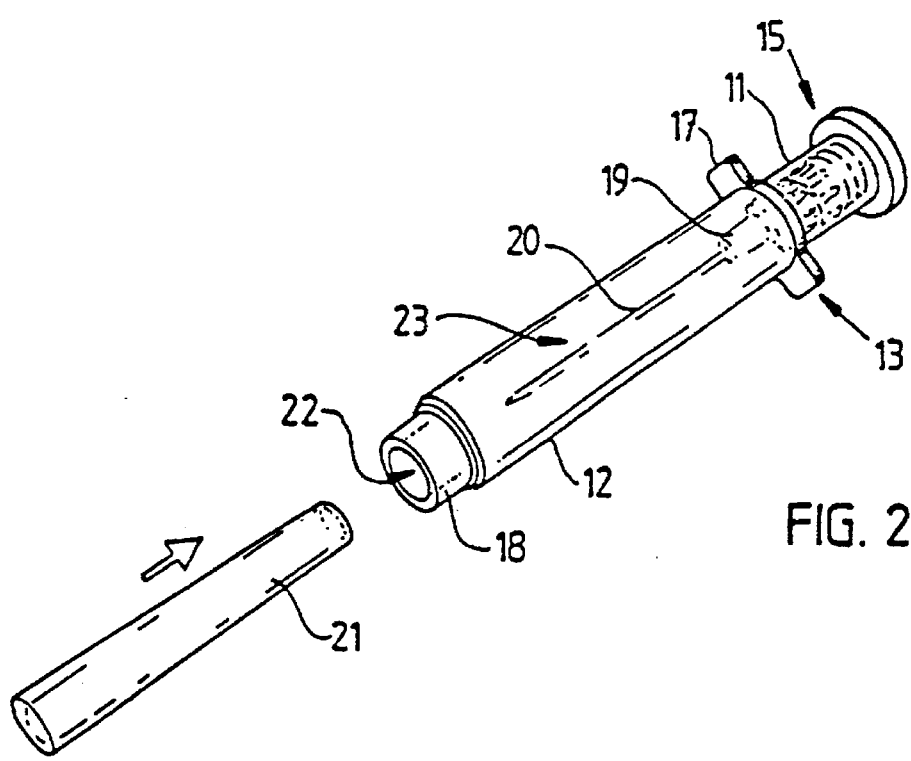

FIG. 2 shows syringe 10 after the medicament has been injected into a patient. The needle 20 and locking element 19 are withdrawn into evacuated chamber 23 in the plunger 11 by the action of the vacuum within the plunger (the process by which this occurs will be described below in relation to FIGS. 3 to 8). Protective cover 21 is then inserted into the opening 22 through which locking element 19 previously protruded to close off the opening. This extra security feature is better illustrated in FIG. 9. The protective cover 21 is shaped and proportioned so that it will sit tightly over locking element 19 and remain in place over the needle 20 prior to use but will also fit tightly into opening 22 when that is created after use of the syringe to seal that opening.

Figure 3:
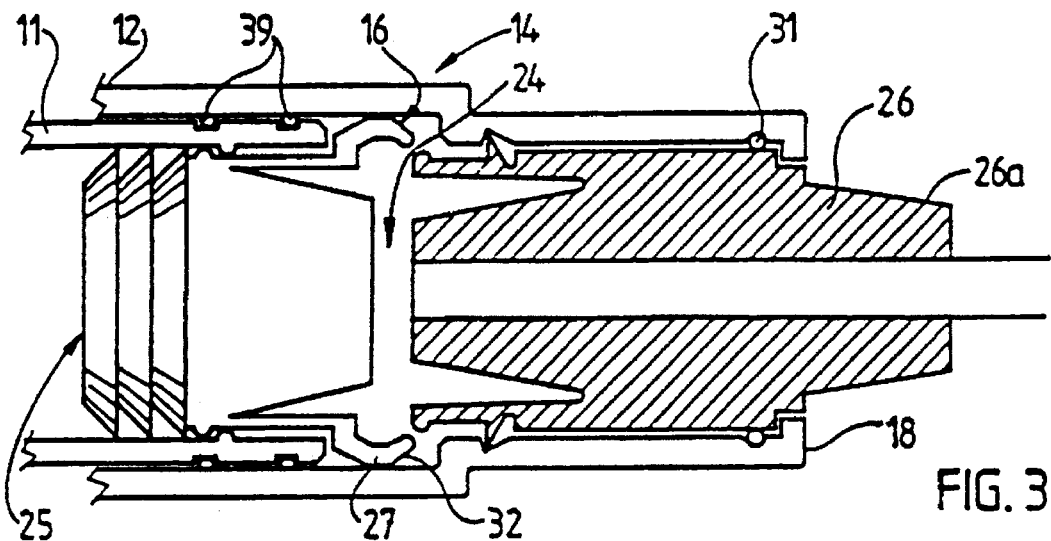
FIGS. 3 to 8 are partial longitudinal cross-sectional views through the distal end of the barrel of the syringe shown in FIGS. 1 and 2 (without a needle) illustrating the steps in the retraction process.

FIG. 3 shows the final stage of the injection process where the distal end 16 of the plunger 11 approaches the distal end 14 of the barrel 12. The space 24 (containing the medicament) within the barrel 12 is very small as most of the medicament has been injected into the patient through the needle 20. Retractable needle attachment member 26 has a coupling portion 26a to which the locking element 19 (here a conventional luer lock) is attached in the conventional manner is also shown. Gripping means 25 which are adapted to engage needle attachment member 26 are located at the distal end 16 of the plunger 11 and constitute the closure of evacuated chamber 23 therein. "O" rings 39 are fitted around the distal end 16 of the plunger 11.

Figure 4:
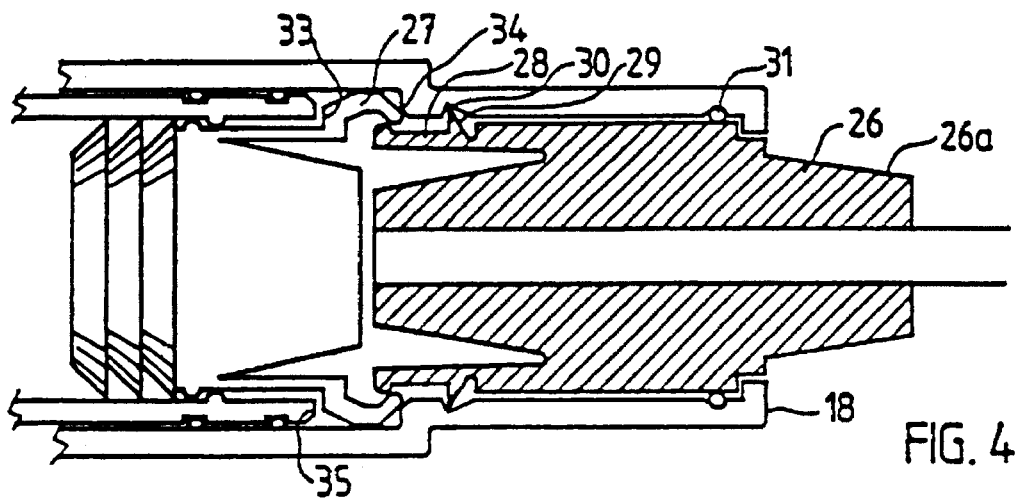

As shown in FIG. 4, as gripping means 25 approaches needle attachment member 26, claw member 27 (which is one of a plurality of circumferentially spaced claw members on gripping means 25) abuts finger 28 (which is one of a plurality of circumferentially spaced fingers on needle attachment member 26). Each claw member 27 has a leading camming surface 32 and a trailing shoulder 33. The trailing shoulder 33 engages the distal face 35 of the plunger 11 so that as the plunger is pushed in the distal direction to expel the medicament, the gripping means 25 travels with it in the distal direction until the camming surface 32 abuts the surface 34 on the inside of the retaining shoulder 18.

The action of claw member 27 on finger 28 pushes it inwardly against the main portion of needle attachment member 26. As force in the distal direction is maintained on the plunger 11, claw member 27 starts to move past finger 28. This is best seen in FIG. 5.

Each of the circumferential fingers 28 is outwardly biased and has a locking projection 29 thereon which engages with an annular shoulder 30 on retaining shoulder 18. Retaining shoulder 18 is simply a moulded extension of barrel 12 therefore this effectively holds the needle attachment member 26 at the distal end 14 of barrel 12 so that medicament may be delivered from the space 24 in the barrel 12 through a bore in needle attachment member 26 into the needle 20 and thence into the patient. An O-ring 31 provides a seal around the needle attachment member 26 to prevent leakage of the medicament from the barrel 12.

Figure 5:
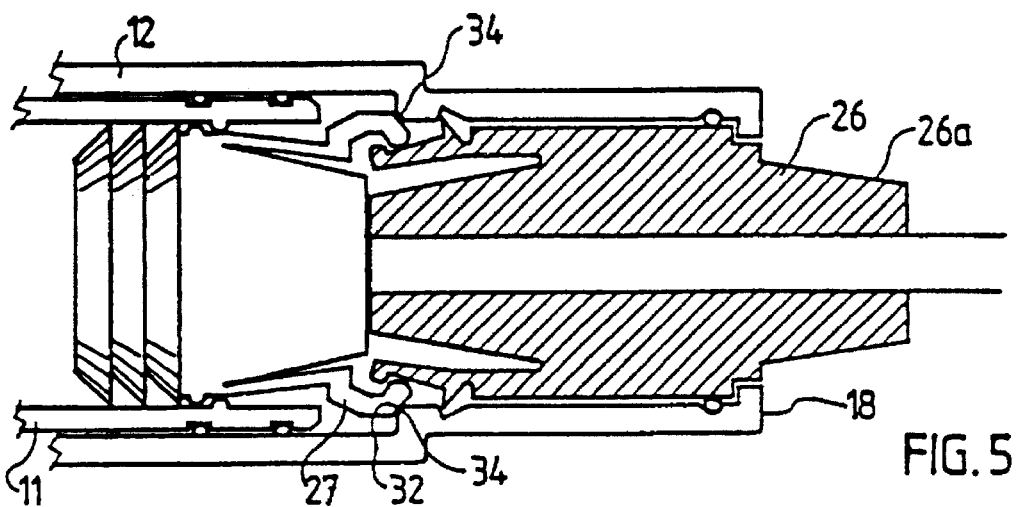
Figure 6:
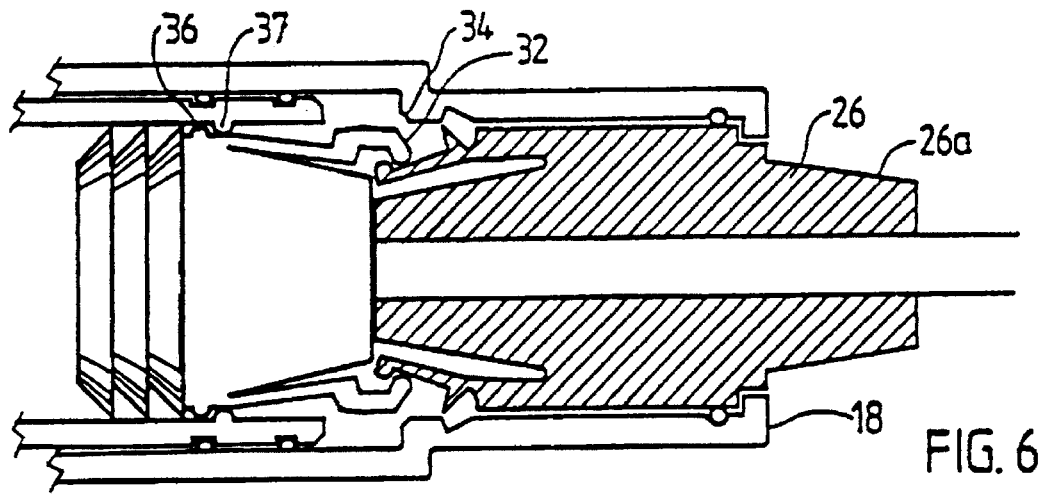
Figure 7:
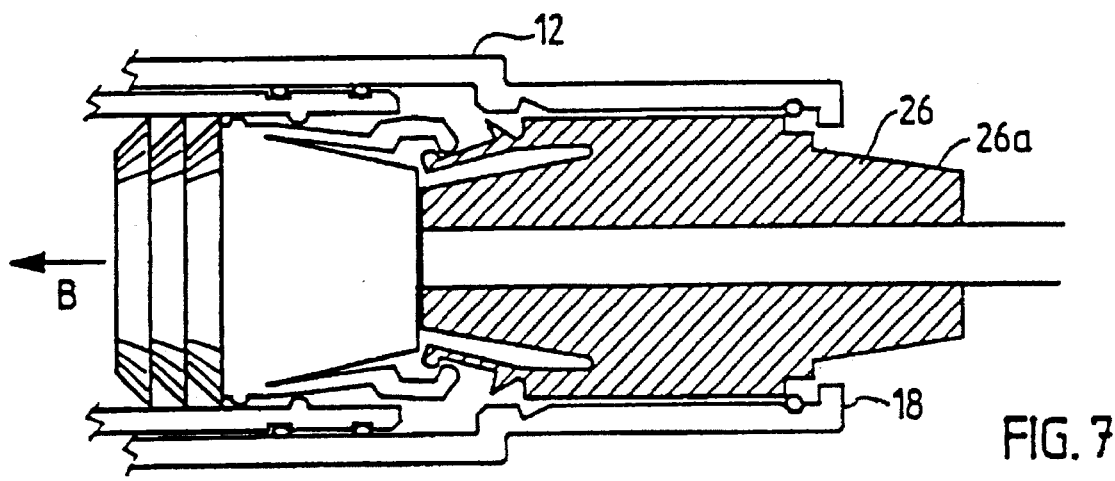
Figure 8:
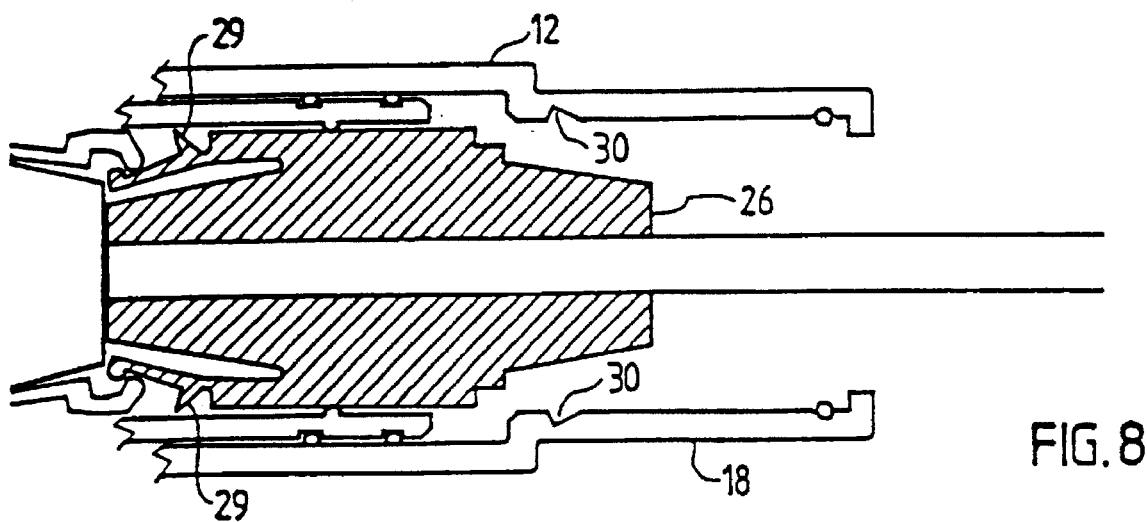
Figure 9:
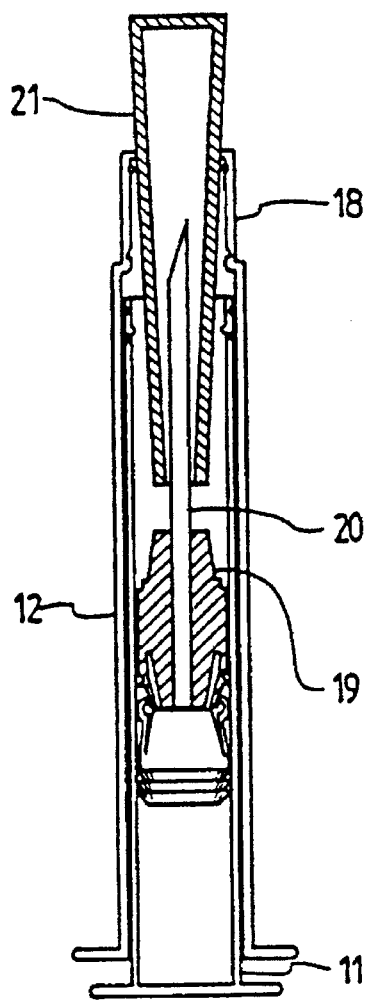
FIG. 9 is a longitudinal cross-sectional view of the syringe shown in FIGS. 1 and 2 illustrating the use of the protective cap to close the opening in a used syringe, and, FIG. 10 as a view similar to FIG. 3 showing the action of the locking projections in response to a resistive force of the skin of the user at the start of the injection process.

Referring to FIGS. 5 and 6, it can be seen that with further movement of the plunger 11 in the distal direction (to fully discharge the contents of the syringe) the camming surface 32 of claw member 27 abuts surface 34 which causes the claw member 27 to bend inwardly. This results in the end of the claw member 27 engaging finger 28 on the needle attachment member 26 and in projection 29 fully disengaging shoulder 30 on the retaining shoulder 18. The needle attachment is, therefore, no longer anchored to the barrel 12, but is attached to the gripping means 25 which form the distal closure of evacuated chamber 23. Since the inward bending of claw member 27 also disengages trailing shoulder 33 from the distal face 35 of the plunger 11, the gripping means 25 is drawn by the vacuum in the direction of arrow B into the evacuated chamber 23 in the plunger 11. As the needle attachment means 26 now engages the gripping means 25, it and the needle 20 attached thereto by locking element 19 are also drawn into the evacuated chamber 23 in the plunger 11. FIG. 8 illustrates the needle 20 as it is retracting and reference once again to FIG. 2 shows the final position of the needle 20.

In order to maintain a suitable vacuum in the chamber 23, it is preferred that the plunger 11 be made of a polymeric material capable of holding a vacuum for a long period, such as polyethylene terephthalate (PET). Alternatively, the plunger may be made of a material such as polypropylene or other conventional materials which will hold a vacuum for 3 to 5 days. If the latter materials are used it is preferred to pack the syringe in a barrier bag which will maintain a vacuum for a long period in and around the syringe. Suitable bags are well known to those skilled in the art.

The walls of chamber 23 (the interior walls of plunger 11) may be equipped with annular beading (not shown) to engage the annular beading 36 on the gripping means 25 to hold the retracted gripping means and the needle attached thereto in position within the plunger 11. Alternatively, the arrangement illustrated in FIG. 9 where the protective cap 21 is jammed into opening 22 covering the needle 20 within the chamber 23 and preventing it from moving in such a way that it could protrude from the opening 22 may be used.

The mechanism illustrated in FIGS. 3 to 8 may also be used in larger or smaller syringes than the syringe illustrated and in syringes where the retaining shoulder is off centre using the same size needle attachment means (but varying the size and/or shape of the gripping means) so that a standard needle can always be used.

The plunger 11 may optionally be equipped with annular beading 37 so that should the vacuum fail the beading 37 and the beading 36 on the gripping means 25 will engage on manual retraction of the plunger so that the needle 20 can be retracted manually into the barrel 12. This is a useful back-up system and provides an additional security feature.

Figure 10:
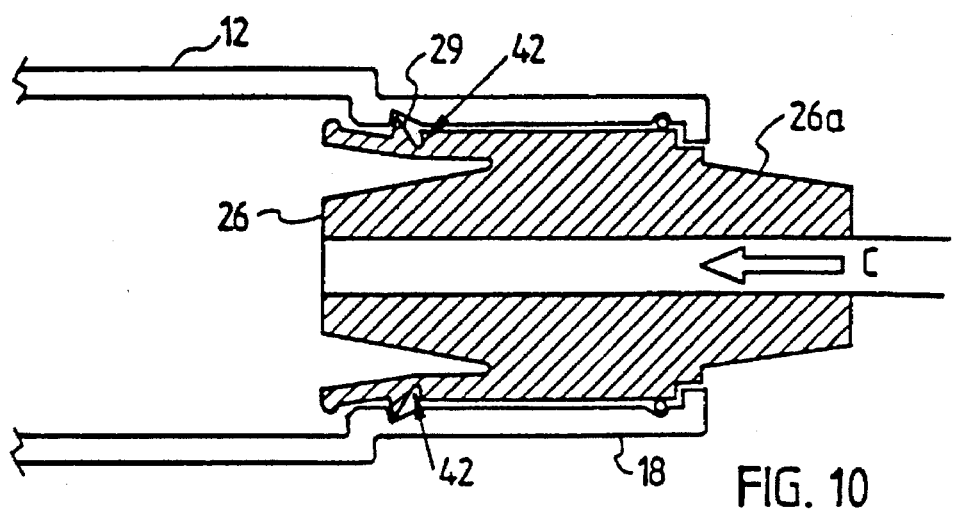

FIG. 10 shows the action of the locking projections 29 in response to the resistive force of the skin in the direction of arrow C. The pivot point 42 is close to the locking projections 29 so that the longitudinal load in the direction of arrow C forces the locking projections 29 outwards rather than inwards. The needle 20 has been omitted for the sake of clarity.

It will be appreciated from the foregoing that the present invention provides a safety syringe which is simple and cheap to manufacture and which can be equipped with a needle attachment member having the normal luer lock fitment and hence, can be used in place of a conventional hypodermic syringe. There are no manual steps necessary to retract the needle so operation of the syringe is no more difficult or time-consuming than a conventional syringe. Furthermore, since retraction of the needle is automatic once the contents of the syringe have been expelled the operator is not exposed to the risk of puncture injuries by the used needle and the needle cannot be used again. This greatly reduces the risk of accidentally contracting diseases from the infected blood of a patient.

It will also be appreciated that while a specific form of the invention has been discussed above by way of illustrative example of the present invention, many other variations and modifications thereto will be apparent to those skilled in the art without departing from the broad ambit and scope of the invention as defined in the appended claims.

I claim:

1. A syringe for administering medicaments comprising:
   an elongated barrel for holding a said medicament, said barrel having a proximal end and distal end;
   a hollow plunger having a closed proximal end protruding from the proximal end of said barrel and a distal end located within said barrel, said plunger being slidably mounted in said barrel and having vacuum means in its interior;
   a retractable needle attachment member for supporting a hypodermic needle, said needle attachment member including releasable retaining means cooperable with means on said barrel to retain said needle attachment member at said distal end of said barrel;
   gripping means for gripping and withdrawing said needle attachment member into said plunger, said gripping means closing said distal end of said plunger, said gripping means cooperating with said distal end of said plunger so that said gripping means is retained at said distal end of said plunger; and
   abutment means within said barrel in the path of movement of said gripping means, said abutment means being engageable by said gripping means upon a predetermined movement of said plunger towards said needle attachment member, said engagement causing said gripping means to be reduced in radial dimensions so as to be disengaged from said distal end of said plunger, said abutment means further urging said gripping means into engagement with said retaining means of said needle attachment member such that said gripping means grips said retaining means and caused said retaining means to release said needle attachment member from engagement with said barrel to permit said needle attachment member to be withdrawn by said gripping means into the interior of said plunger by the vacuum within said plunger.

2. A syringe according to claim 1 wherein said needle attachment member is located in a retaining shoulder which protrudes from said distal end of said barrel and includes a portion for releasable attachment of a luer lock hypodermic needle whereby medicament can be expelled through said needle attachment member and thence through said needle as said plunger moves toward said distal end of said barrel.

3. A syringe according to claim 2 wherein said needle attachment member is operatively secured in said retaining shoulder by said releasable retaining means which comprises a releasable catch which is released when said plunger is pushed home to expel substantially said medicament from said barrel through said needle.

4. A syringe according to claim 3 wherein said catch further comprises an annular shoulder on an internal wall of said retaining shoulder which cooperates with an outwardly biased finger protruding from a side wall of said needle attachment member, said outwardly biased finger comprising said releasable retaining means.

5. A syringe according to claim 4 wherein said biased finger includes a protrusion that engages said annular shoulder and a portion of reduced thickness distally adjacent said protrusion constituting a pivot point for said biased finger so that said biased finger bends outwardly maintaining the engagement of said projection with said needle attachment means is subject to force in the proximal direction.

6. A syringe according to claim 4 wherein said gripping means includes a catch release mechanism adapted to engage said biased finger on said needle attachment member and release said biased finger from engagement with said annular shoulder so that said needle attachment member engages said gripping means and is released from said retaining shoulder, whereby said gripping means disengages from said distal end of said plunger and said gripping means in operative engagement with said needle attachment member is retracted into the interior of said plunger by the vacuum within said plunger.

7. A syringe according to claim 6 wherein said catch release mechanism comprises a claw member including a leading camming surface said shoulder, said trailing shoulder normally engaging a distal face of said plunger and said camming surface being adapted to abut an inside surface of said retaining shoulder, whereby said claw member is urged to bend inwardly when said camming surface abuts said retaining shoulder inside surface to engage said biased finger and causing said trailing shoulder to disengage from said distal face of said plunger.

8. A syringe according to claim 1 wherein said gripping means includes a first annular beading adjacent its proximal end and said plunger includes a second annular beading on its inside surface adjacent said distal end of said plunger, wherein on manual withdrawal of said plunger in the proximal direction said second annular beading on said plunger engages said first annular beading on said gripping means allowing said gripping means and operatively engaged said needle attachment means to be withdrawn into said barrel in the event that the vacuum retraction fails.

9. A syringe comprising:
an elongated barrel having a proximal end and a distal end;
a hollow plunger having a closed proximal end protruding from said proximal end of said barrel and a distal end located within said barrel, and plunger being slidably mounted in said barrel and having a vacuum in its interior;
a retractable needle attachment member for supporting a hypodermic needle;
catch means for releasably holding said needle attachment member at said distal end of said barrel, said catch means including at least one finger on said needle attachment member biased into engagement with portion of the interior of said barrel;
gripping means for gripping and withdrawing said needle attachment member, said gripping means closing said distal end of said plunger and having a plurality of retaining and gripping members cooperable with the distal end of said plunger for retaining said gripping means at said distal end of said plunger; and
abutment means on a side wall of said barrel in the path of movement of said gripping members, whereby when said plunger is advanced and said gripping means approaches said needle attachment member, said abutment means is engaged by said retaining and gripping members of said gripping means and urges said gripping members inwardly to reduce the radial dimensions of said gripping means and thus disengages said gripping means from said distal end of said plunger, and wherein at least one said retaining and gripping member on said inward movement engages and deflects said at least one finger to release said catch means and permit said needle attachment member to be withdrawn by said gripping means into the interior of said plunger by the vacuum within said plunger.

10. A syringe according to claim 9 wherein said abutment means comprises an annular shoulder on an internal side wall of said barrel.

11. A syringe according to claim 9 wherein said finger includes a projection and wherein said portion of said barrel includes an annular recess on an internal side wall of said barrel which receives said projection on said finger.

12. A syringe according to claim 11 wherein said needle attachment member includes a plurality of circumferentially spaced said fingers and wherein said retaining and gripping members of said gripping means are engageable with respective said fingers.

13. A syringe comprising:
an elongated barrel having a proximal and a distal end and a cylindrical side wall;
a hollow tubular plunger having a closed proximal end protruding from said proximal end of said barrel and a distal end located within said barrel, said distal end having an annular end surface, said plunger being slidably mounted in said barrel and having a vacuum in its interior;
a retractable needle attachment member for supporting a hypodermic needle;
catch means for releasably holding said needle attachment member at said distal end of said barrel, said catch means including catch members on said needle attachment member cooperable with an annular recess in said cylindrical wall of said barrel;
gripping means for gripping and withdrawing said needle attachment member, said gripping means closing said distal end of said plunger and having a plurality of gripping members, said gripping members cooperating with said annular end face of said plunger to retain said gripping means at said distal end of said plunger, said gripping members further including camming means for causing deflection of said gripping members; and
an abutment shoulder on said side wall of said barrel in the path of movement of said gripping members towards said distal end of said barrel, whereby when said plunger is advanced and said gripping means approaches said needle attachment member, said abutment shoulder is engaged by said camming means of said gripping members to cause said gripping members to be urged inwardly to disengage said gripping means from said distal end face of said plunger, and said abutment shoulder further causing said gripping members on said inward movement to engage and deflect said catch members to release said catch means and permit said needle attachment member to be withdrawn by said gripping means into the interior of said plunger by the vacuum within said plunger.

* * * * *